United States Patent [19]

Burger

[11] Patent Number: 4,767,330

[45] Date of Patent: Aug. 30, 1988

[54] APPARATUS FOR FABRICATING TOOTH ARRANGEMENT MODELS

[75] Inventor: Bernd Burger, Alling, Fed. Rep. of Germany

[73] Assignee: ESPE GmbH Fabrik pharmazeutischer Präparate GmbH, Seefeld, Fed. Rep. of Germany

[21] Appl. No.: 857,930

[22] Filed: Apr. 30, 1986

[30] Foreign Application Priority Data

Apr. 30, 1985 [DE] Fed. Rep. of Germany ....... 3515510

[51] Int. Cl.⁴ ............................................. A61C 11/00
[52] U.S. Cl. ...................................... 433/213; 433/74
[58] Field of Search ............... 433/74, 213; 252/62.54; 106/35; 524/440

[56] References Cited

U.S. PATENT DOCUMENTS

| | | | |
|---|---|---|---|
| 2,947,646 | 8/1960 | Devaney | 524/440 X |
| 2,959,832 | 11/1960 | Baermann | 252/62.54 X |
| 2,985,961 | 5/1961 | Schwartz | 433/213 |
| 3,650,032 | 3/1972 | Kestler | 433/53 |
| 4,017,972 | 4/1977 | Glenn | 433/53 |
| 4,174,570 | 11/1979 | Schwartz | 433/74 |
| 4,368,042 | 1/1983 | Felstead et al. | 433/213 |
| 4,494,934 | 1/1985 | Huffman | 433/213 |
| 4,508,506 | 4/1985 | Jackson | 433/74 |
| 4,608,016 | 8/1986 | Zeiser | 433/74 |

FOREIGN PATENT DOCUMENTS

| | | |
|---|---|---|
| 0044223 | 1/1982 | European Pat. Off. . |
| 3214856 | 10/1983 | Fed. Rep. of Germany ...... 433/213 |
| 3315870 | 11/1984 | Fed. Rep. of Germany ...... 433/213 |

Primary Examiner—David H. Corbin
Assistant Examiner—Anthony Knight

[57] ABSTRACT

An apparatus for the fabrication of models of teeth and their arrangement. The apparatus includes an approximately U-shaped tooth arrangement support, and a base plate to which the support is detachably connected. This connection between the tooth arrangement support and the base plate is ensured by magnetic forces.

12 Claims, 2 Drawing Sheets

APPARATUS FOR FABRICATING TOOTH ARRANGEMENT MODELS

BACKGROUND OF THE INVENTION

1. Field of the Invention

The present invention relates to an apparatus for the fabrication of models of teeth and their arrangement, especially so-called serrated models, with the teeth being detachably connected, either individually or in groups, with a base plate.

2. Description of the Prior Art

For various dental work, it is necessary to have a true-to-size tooth and jaw model, a so-called master model. To produce such a model, a plaster of Paris imprint is taken of the jaw of the patient. The tooth arrangement model that is obtained is generally secured to a base plate, which is generally also made of plaster of Paris. For certain dental work, for example when fitting crowns, caps, or bridges, it is desirable to be able to remove individual teeth, or groups of teeth in the form of segments, from the base plate, and to be able to accurately reinsert them after the work is complete. For this purpose, with conventional models, pins, so-called dowel pins, are provided, one end of which is fixedly connected to the tooth arrangement segments, with the other free end fitting into corresponding holes provided in the base plate. When the dowels pins are withdrawn from the holes, relatively high frictional forces result, preventing the segments from accidentally coming loose from the base plate.

Unfortunately, this dowel pin technology has, among others, the following drawbacks:

1. The pins must be disposed exactly parallel to one another, since this is the only way to provide for a problem-free removal and reinsertion of tooth arrangement segments. Relatively complicated and expensive pin-setting apparatus is used for placing the pins.

2. A precise seating of the individual tooth arrangement segments can be achieved only with difficulty, especially when the pins and holes become worn due to frequent removal.

3. Generally, the base plate can be used only once, since the pins and holes are precisely disposed relative to one another, and in practice it is not possible to insert pins into a tooth arrangement in such a manner that they will fit exactly in an existing base plate that is already provided with holes.

4. Models for crowns and bridges are generally made of wax. With all models where the tooth arrangement is held on the base plate by frictional forces, there exists the serious drawback that in order to remove the segments, relatively high frictional forces must be overcome. In so doing, tilting is unavoidable, so that damage to the parts that are modeled in wax can easily occur.

Attempts have already been made with such tooth models to dispense with the use of dowel pins. Without exception, all of the proposals for realizing this possibility also assured connection between the tooth arrangement and the base plate by using frictional forces. For example, European Patent application No. 44 223 discloses such a model, the tooth arrangement of which, on the underside, is provided with a pattern of parallel zig-zagged ribs in grooves. The upper surface of the base plate is provided with a pattern that is complementary to the pattern of the tooth arrangement. When the tooth arrangement and base plate are placed together, the ribs in grooves mesh with one another, thus assuring connection of the two parts via frictional forces. However, this proposal also results in the aforementioned difficulties. In particular, there exists the danger outlined above in paragraph number 4, namely damage to the model parts made of wax when the individual tooth segments are removed from the base plate.

An object of the present invention is to provide an apparatus for the fabrication of tooth arrangement models having removable tooth arrangement segments, with such segments being adapted to be secured to the base plate in a simple and precise manner without the seating of the segments becoming loose after repeated removal, and without there existing the danger of damaging models made of wax.

BRIEF DESCRIPTION OF THE DRAWINGS

This object, and other objects and advantages of the present invention, will appear more clearly from the following specification in conjunction with the accompanyin schematic drawing, in which.

SUMMARY OF THE INVENTION

Figures 1, 2:
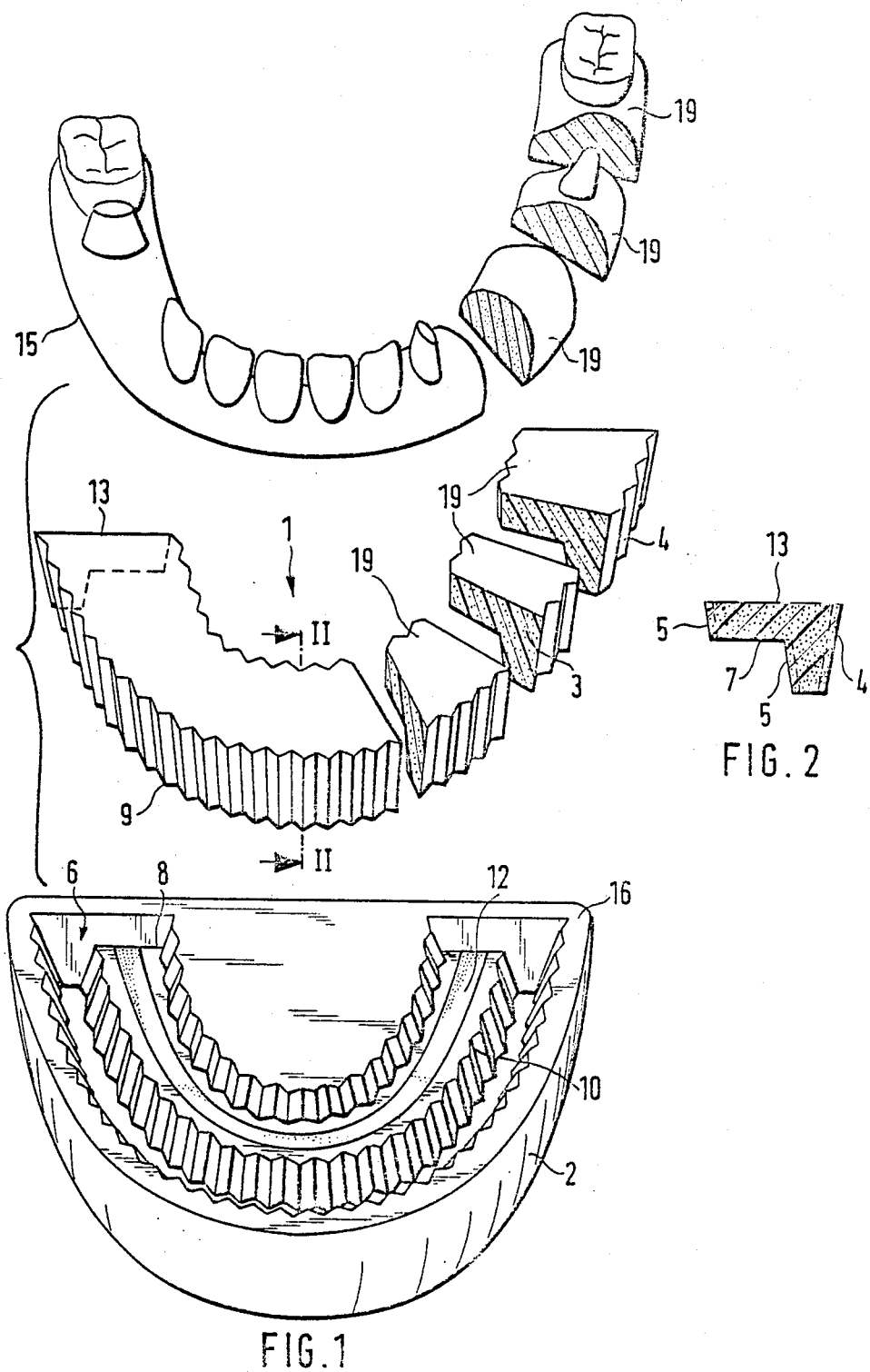
FIG. 1 is an exploded, perspective view of one exemplary embodiment of the inventive apparatus in conjunction with a tooth arrangement.
FIG. 2 is a cross-sectional view of the tooth arrangement support and is taken along the line II—II in FIG. 1.

Pursuant to the present invention, the aforementioned object is realized by an apparatus for the fabrication of models of teeth and their arrangement, which apparatus comprises: a base plate, and a tooth arrangement support, especially approximately a U-shaped support, that is detachably connected with the base plate via magnetic forces.

For this purpose, both the tooth arrangement support and the base plate respectively contain magnetic material. The term "magnetic material" means that at least one of the two parts contains permanently magnetic material, while the other part contains magnetizable or also permanently magnetic material.

The magnetic materials are preferably in the form of filled synthetic materials, which have the advantage that they can be easily shaped and worked. Fillers include conventional magnetic materials in pulverious form, such as iron, cobalt, nickel, alloys thereof, ferrites, etc.

The use of magnetic forces to ensure the connection between the tooth arrangement support and the base plate offers the advantage that the force that effects the connection always remains constant, and is not adversely affected by the wearing away of material. Since frictional forces are to a large extent eliminated, it is also not necessary to have to carry out sudden or jerky movements in order to overcome such forces, which movements otherwise easily lead to tilting and hence to damage of the wax parts. Furthermore, multiple use of the base plate is possible without difficulty. Finally, the inventive apparatus offers the advantage that it can be produced in a time-saving manner.

Pursuant to one preferred embodiment of the inventive apparatus, the tooth arrangement support essentially comprises a U-shaped member that contains magnetic material and is provided with side walls that extend conically toward one another. The base plate has a recess that is complementary to the member, with the surface region of the recess also being provided with magnetic material. This conical member facilitates the precise positioning of the tooth segments relative to the base plate. The conical cross-sectional shape of the member assures that when the segments are removed, only negligibly low frictional forces occur, resulting in the aforementioned advantages.

The member is expediently provided with a shoulder that extends parallel to, or at an acute angle to, the plane of the base plate; this shoulder corresponds to an offset portion in the base plate. Preferably, on the inner wall of the base plate, the offset portion does not extend parallel to the plane of the base plate, but rather extends at a slight angle of 5° to 10° toward the center of the base plate, for example, so that certain tolerances can be more easily compensated for when the tooth arrangement support and the base plate are fitted. In conformity with this slope, the shoulder of the member of the tooth arrangement support must also be slanted. Permanent magnets are preferably inserted in the region of the offset portion of the base plate. These magnets ensure connection with the member, which preferably comprises a synthetic material that is filled with magnetic material.

In order to facilitate positioning of the segments relative to the base plate, and to increase the precision of the fit, ribs are preferably disposed on the conical side walls of the member. These ribs extend parallel to one another, and at right angles to the upper surface of the member. In a similar manner, grooves that are complementary to the ribs are then provided on the walls of the recess in the base plate.

Pursuant to a further preferred embodiment of the present invention, slots or bores are provided on the bottom surface of the base plate; the tooth arrangement support can then be screwed to the base plate from below via the slots or bores. This offers the advantage that various work, especially milling operations, are then possible directly on the tooth arrangement model.

It is particularly advantageous to embody the magnet that is inserted in the base plate in such a way that it can be removed from below. The magnet can then be held securely in position by screws, a push button type of connection, or a type of bayonet closure, for example. As a result, after this magnet has been removed, the removal of the tooth arrangement segments is particularly simple. Furthermore, in the event that the base plate becomes damaged, the relatively expensive magnet can be removed and placed in another base plate.

It has furthermore proven to be advantageous, during casting or pouring of the root member or tooth arrangement support, to close off the slots or bores on the underside of the base plate by a space retainer, for example of silicon rubber, to thereby make it impossible for the flowable material to escape.

Finally, it is possible to insert on the underside of the base plate, in the central region thereof, a magnet with which the apparatus can be secured to an articulator.

The inventive apparatus is expediently fabricated in various sizes to permit adaptation to the dimensions of the upper and lower jaw.

Further advantageous features of the present invention will be described in detail subsequently.

DESCRIPTION OF PREFERRED EMBODIMENTS

Referring now to the drawings in detail, FIG. 1 shows a support 1 for a tooth arrangement. This support 1 essentially comprises an approximately U-shaped member 3, the side walls 4, 5 of which extend conically downwardly toward one another. The side walls 4, 5 are provided with ribs 9 that extend parallel to one another, and substantially at a right angle to the upper surface 13 of the tooth arrangement support 1.

The cross-sectional view of FIG. 2 shows that the tooth arrangement support 1 is provided with a shoulder 7 on the inner side wall 5, so that overall, the support 1 has an approximately L-shaped cross section.

When using the inventive apparatus in practice, the actual tooth arrangement 15, which is obtained by filling the jaw casting or mold, is secured to the support 1. This is expediently effected via laminar adhesion by means of a quick-setting adhesive. The arrangement of the support and tooth arrangement as necessary, then can be divided by vertical saw cuts into segments 19 of individual teeth or groups of teeth.

To produce the tooth arrangement support 1, generally a flowable, curable monomer and/or prepolymer can be used that has little contraction and is filled with a magnetic or magnetizable metal powder.

A U-shaped recess 6 is provided in the base plate 2 of FIG. 1. This recess 6 is complementary to the shape of the member 3, i.e. the side walls of the recess 6 extend conically downwardly toward one another. An offset portion 8 on the inner wall of the recess 6 corresponds to the shoulder 7 of the member 3. Furthermore, the outer walls of the recess 6 are provided with grooves 10 that extend parallel to one another and are disposed substantially at a right angle to the upper surface 16 of the base plate 2. These grooves 10 serve to receive the ribs 9. Thus, there results on the side walls of the member 3 and the recess 6 respective zig-zagged patterns. These complementary patterns facilitate an exactly fitting insertion of the tooth arrangement support 1 into the recess 6. Due to the conical cross-sectional shape of the member 3 and of the recess 6, only very slight frictional forces result when the support 1 is withdrawn from the recess. Connection between the base plate 2 and the member 3, which comprises magnetic material, is assured by flat magnets 12 that are disposed in the region of the offset portion 8.

To produce the inventive apparatus, one starts with a blank for the base plate 2. The recess 6 is provided in the base plate 2 by machining the latter. By using appropriate molds, it would also be possible to produce the base plate in a single operation via injection molding or some similar molding technique.

To produce the tooth arrangement support 1, the aforementioned flowable material is then poured into the recess 6, where it is allowed to cure. Since the pouring or casting process can be repeated as often as desired, a multiple reuse of the base plate is assured. Alternatively, it would also be possible to produce the tooth arrangement support 1 in a separate process, such as by inJection molding or some other precise molding technique. So that the polymerized tooth arrangement support 1 can be easily removed from the base plate 2, the surface of the latter should be as smooth as possible. Examples of materials that can be used for the base plate include plastics and metals. For example, the base plate could be made of polyoxymethylene (Delorin), polyethylene, polypropylene, polyamide resin, acrylic resin (plexiglass), polyvinyl chloride, brass, and aluminum.

One example of an adhesive that would be suitable for adhesively mounting the tooth arrangement on the support 1 is a cyanoacrylate adhesive.

Figure 3:
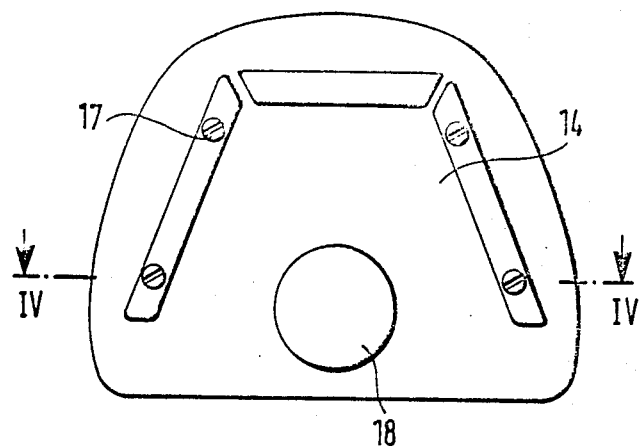
FIG. 3 is a bottom view of a base plate showing the screw connection of the tooth arrangement support.
Figure 4:
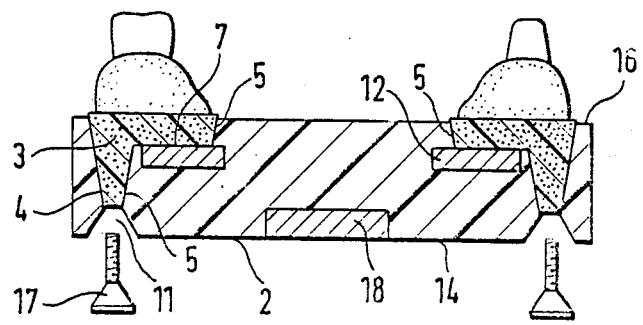
FIG. 4 is a cross-sectional view taken along the line IV—IV in FIG. 3.

In the embodiment illustrated in FIGS. 3 and 4, the bottom surface 14 of the base plate 2 is provided with slots 11 having a conical cross section. Via these slots 11, the tooth arrangement support 1 can be secured to the base plate 2 from below via screws 17. This makes it possible to have a rigid and fixed connection between the base plate 2 and the tooth arrangement support 1, so that milling work required on individual parts can be carried out directly on the inventive apparatus without it being necessary to remove the individual tooth segments and clamp them separately.

Inserted in the bottom surface 14 of the base plate 2, in the central region thereof, is a magnet 18 with the aid of which the inventive apparatus can be mounted on an articulator.

The following example illustrates one exemplary embodiment of the present invention.

EXAMPLE 25 g fine iron dust (less than 100 μm, average particle size approximately 15 μm) are worked into a homogeneous mixture with 10 g 2,2-bis-[p-(β-hydroxyethoxy)-phenyl]-propane-bis β-ethyleneiminobutyrate (polymerizable prepolymer) and 300 mg 2-ethylhexyl-ethyl-sulfonium-isobutyronitrilefluoroborate (polymerization initiator). As soon as these materials have been mixed together, the very flowable mixture is poured into the recess 6 of a polypropylene base plate 2, where it is allowed to set. The material of the mixture remains flowable for approximately 5 minutes at room temperature, and is set or cured after approximately 15 minutes. After it has set, the finished tooth arrangement support 1 is removed from the base plate 2. The upper surface 13 of the support 1 is laminarly secured with a cyanoacrylate adhesive to a tooth arrangement model 15 made of gypsum or plaster of Paris. The finished arrangement, which comprises the tooth arrangement and the tooth arrangement support, is separated by vertical cuts into individual tooth segments 19 that with the aid of the base plate 2 can easily be combined again to form a complete tooth arrangement model.

The present invention is, of course, in no way restricted to the specific disclosure of the specification and drawings, but also encompasses any modifications within the scope of the appended claims.

What I claim is:

1. An apparatus for the fabrication of models of teeth and their arrangement, comprising:
   a base plate;
   a tooth arrangement and support, the latter being detachably connected and held together with said base plate; and
   rigid magnetic tooth arrangement carrier means that provide magnetic forces essentially to hold said tooth arrangement therewith without any dowel-pin problematic arrangment therebetween.

2. An apparatus according to claim 1, in which said tooth arrangement and support being collectively approximately U-shaped.

3. An apparatus according to claim 1, in which said support essentially comprises a member having an upper surface for supporting a tooth arrangement, a bottom surface, and side walls that extend conically toward one another as they approach said bottom surface; said member contains magnetic material; said base plate is provided with a recess that is complementary in shape to said member for accommodating the latter; in a surface region thereof that faces said member, said recess is provided with magnetic material for cooperating with said magnetic material of said member to effect said magnetic connection between said tooth arrangement and said support relative to said base plate.

4. An apparatus according to claim 3, in which said magnetic material of said base plate is in the form of a permanent magnet.

5. An apparatus according to claim 4, in which said permanent magnet is removably secured to said base plate, and can be removed from the latter from that side thereof remote from said support.

6. An apparatus according to claim 3, in which said member is provided with a shoulder that extends substantially parallel to said upper surface of said member; and in which said recess in said base plate includes an offset portion that corresponds to said shoulder.

7. An apparatus according to claim 6, in which said magnetic material of said base plate is disposed in the region of said offset portion of said recess.

8. An apparatus according to claim 3, in which said side walls of said member are provided with ribs that are disposed parallel to one another, and at a right angle to said upper surface of said member; and in which said recess of said base plate is provided with grooves that are complementary to said ribs.

9. An apparatus according to claim 3, in which said base plate is provided with opening means via which said support can be screwed to said base plate from that side of the latter remote from said support.

10. An apparatus according to claim 3, in which at least the magnetic material of said member is a synthetic material that is filled and mixed together with a magnetic material incorporated therewith.

11. An apparatus according to claim 3, in which the central region of that surface of said base plate remote from said tooth arrangement is provided with a magnet.

12. An apparatus according to claim 6, in which said member is approximately U-shaped, and has an approximately L-shaped cross-section.

* * * * *